United States Patent [19]

Casara et al.

[11] Patent Number: 5,416,076
[45] Date of Patent: May 16, 1995

[54] S-ADENOSYL METHIONINE DECARBOXYLASE INHIBITORS

[75] Inventors: Patrick Casara, Ittenheim; Charles Danzin, Strasbourg, both of France

[73] Assignee: Merrell Dow Pharmaceuticals Inc., Cincinnati, Ohio

[21] Appl. No.: 896,733

[22] Filed: Jun. 9, 1992

Related U.S. Application Data

[63] Continuation of Ser. No. 773,746, Oct. 10, 1991, abandoned, which is a continuation of Ser. No. 378,737, Jul. 12, 1989, abandoned, which is a continuation-in-part of Ser. No. 367,275, Jun. 16, 1989, abandoned.

[30] Foreign Application Priority Data

Jun. 28, 1989 [FR] France .................. 89 401845.6

[51] Int. Cl.$^6$ ..................... A61K 31/70; C07H 19/167
[52] U.S. Cl. ..................... 514/46; 536/27.31
[58] Field of Search ................ 536/27.31; 514/46

[56] References Cited

U.S. PATENT DOCUMENTS 4,134,918  1/1979  Bey et al. ............... 536/27.31
4,794,174  12/1988  Secrist, III .............. 536/27.31

OTHER PUBLICATIONS

Davis et al. (1983) Aust. J. Chem., vol. 36, pp. 1623–1627.
Casara et al. (1984) Tetrahedron Letters, vol. 25, No. 18, pp. 1891–1894.
Metcalf et al. (1978) J. Am. Chem. Soc., vol. 100, No. 8, 2551–2553.
Pugh et al. (1982) Biochemistry, vol. 21, 1535–1541.
Minnick et al. (1988) J. Org. Chem., vol. 53, 4952–4561.
Reich et al. (1990) J. Biol. Chem., vol. 265, No. 15, 8966–8970.
Anton et al. (1987) Biochemistry, vol. 26, 6444–6447.
Chang et al, (1976) J. Med. Chem. vol. 14, No. 5, pp. 684–691.
Santi et al. (1987) Biochemistry, vol. 26, 8599–8606.
Casara et al. (1989) J. Am. Chem. Soc., vol. 111, No. 25, pp. 9111–9113.
Bijonti et al, (1990) Antimicro. Agents Chemotherapy, vol. 34, No. 8, 1485–1490.

(List continued on next page.)

*Primary Examiner*—Douglas W. Robinson
*Assistant Examiner*—Gary L. Kunz
*Attorney, Agent, or Firm*—Stephen L. Nesbitt

[57] ABSTRACT

The adenosine derivatives represented by the following formula:

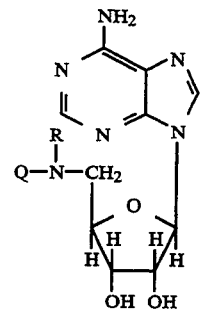

and the pharmaceutically acceptable salts thereof wherein
R is H or $C_1$–$C_7$ alkyl,
Q is the moiety of the formula

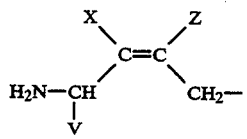

wherein
V is H or —COOH
X is H, F, Cl, Br, and
Z is H, F, Cl, or Br.

These compounds are inhibitors of S-adenosylmethione decarboxylase and are useful for treating parasitic infections.

8 Claims, No Drawings

OTHER PUBLICATIONS

Pegg, Anthony E., et al., *Biochemistry 27*, pp. 1408–1415, (1988).

Chemical Abstracts 100:103834, M. Davis, et al.

Kolb, Michael, et al., *J. Med. Chem. 25*, pp. 550–556 (1982).

Pankaskie, Marvin, et al., *J. Med. Chem. 23*, pp. 121–127 (1980).

J. S. Secrist, III, *Nucleosides & Nucleotides 6*, No. 1–2, pp. 73–83 (1987).

S-ADENOSYL METHIONINE DECARBOXYLASE INHIBITORS

CROSS-REFERENCE TO RELATED APPLICATION

This is a continuation of application Ser. No. 07/773,746, filed Oct. 10, 1991, now abandoned, which is a continuation of application Ser. No. 07/378,737, filed Jul. 12, 1989, now abandoned, which is a continuation-in-part of application Ser. No. 07/367,275, filed Jun. 16, 1989, now abandoned.

This invention relates to novel chemical compounds useful as S-adenosylmethionine decarboxylase inhibitors, to the processes useful for their preparation and/to their use in the treatment of a variety of condition and disease states associated with a rapid proliferation of cell growth.

More specifically, this invention relates to compounds of the formula

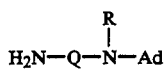

and the pharmaceutically acceptable salts thereof, wherein Ad represents adenosinyl, R is hydrogen or a $C_{1-7}$ alkyl, and Q represents moieties of formulae Ia to Ie, said formulae being depicted as:

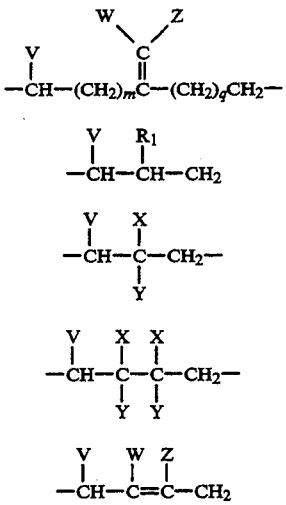

with m being zero or one, q being zero or one with the proviso that the sum of m and q is less than 2, V is H or —COOH,
W is H, F, Cl or Br,
Z is H, F, Cl or Br,
each X and each Y being H or F,
$R_1$ is

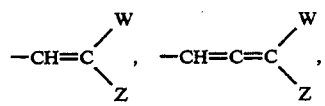

—C≡CH or —CH$_{3-n}$F$_n$ with n being 1, 2 or 3.

Of course, the "$H_2N$—" moiety (which is attached to Q in formula I) is attached to the carbon atom bearing the "V" substituent in each of formulae Ia to Ie (e.g.,

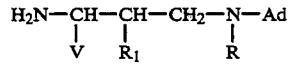

wherein Q is represented by Ib).

The "Ad" moiety (i.e., the adenosinyl moiety comprised of 1H-purine-6-amine attached to β-D-ribofuranosyl) has the structure

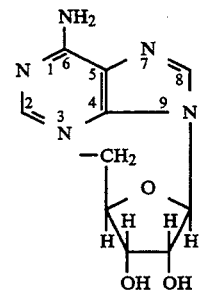

In those instances wherein Q is representative of formula Ia, it is to be noted that only one of the m or q moieties may be one for any given compound. In those instances wherein R is other than H, the $C_{1-7}$ alkyl moiety is preferably methyl and ethyl but all the straight, branched-chain and cyclized manifestations are included with methyl being preferred and ethyl, propyl, isopropyl, butyl, t-butyl, pentyl, hexyl, cyclohexylmethyl and the like being especially included. In those instances wherein Q is representative of formula Ie, it is preferred that said compounds be in their cis-configuration rather than their trans-configuration.

In those instances wherein Q is representative of formula Id the mono-, di-, tri- and tetrafluoro substituted moieties (as well as the unsubstituted moieties) are contemplated. Preferred compounds are those of formula I wherein Q is Ie, are those wherein W and Z are H and V is H or COOH, and R is methyl or ethyl.

Illustrative examples of pharmaceutically acceptable salts of the compounds of this invention are those formed with inorganic acids preferably with hydrochloric, hydrobromic, sulfuric or phosphoric acids and with organic acids such as methane sulfonate, salicylic, maleic, malonic, tartaric, citric and ascorbic acids. These salts may be prepared by standard techniques and procedures well known in the art.

In essence, the preparation of the compounds of formula I may be effected by techniques and chemical processes analogously known in the art; the choice of the specific route being dependent upon the usual factors in pharmaceutical research institutions such as availability and cost of starting materials, time and difficulties in separation and purification of intermediates and final compounds and such other factors well known and generally appreciated by those of ordinary skill in the art.

In general the preparation of the compounds of formula I may be depicted by the reaction sequence of reaction sequence of reaction scheme A, as follows:

Reaction Scheme A

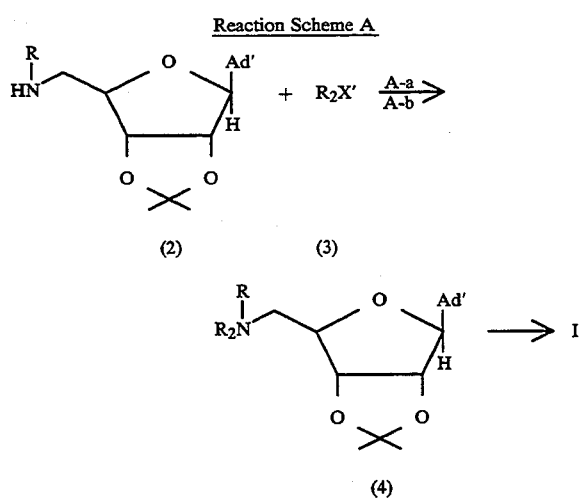

wherein Ad' is adeninyl of the formula

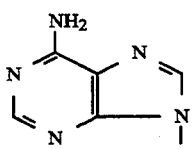

$R_2X'$ is a reactant of the following formulae (3a to 3f).

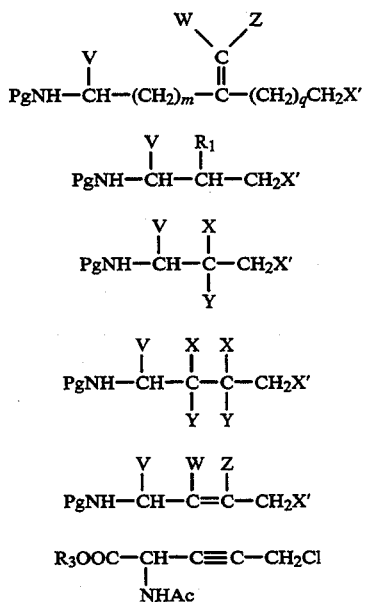

wherein Pg is an N-protecting group, preferably t-butoxycarbonyl (Boc) or phthalimido (Pht) (in which case, of course, the H of the PgNH moiety is not present) and m, n, q, R, $R_1$, V, W, X, Y and Z are as defined in Formula I, and X' is OTF (triflate) or chloro, bromo or iodo, ($R_2$, of course, being the moieties of 3a to 3f attached to the X' moiety), with the exception that in appropriate cases V may be a reaction-protection derivative of the COOH function, preferably a t-butoxy derivative and Ac is an acyl moiety, preferably acetate, and $R_3$ is t-butyl.

In effecting the condensation of reactants 2 and 3 when X' represents a halide conditions A-a are utilized wherein equimolar quantities of the reactants are reacted together in the presence of a base, (preferably potassium carbonate), in a basic solvent, (preferably acetonitrile), at temperatures of about 30° C. to 80° C. When conditions A-b are utilized, i.e., when X' is a triflate, the reactants are heated together at about 30° C. to 80° C. in the presence of a base, (preferably triethylamine), in a basic, solvent, (preferably dimethylformamide). Removal of the N-protecting groups is readily effected by standard techniques, e.g., treatment with 1N sulfuric acid at room temperature for 24–48 hours followed by treatment with an alcohol (preferably ethanol) at about 0° C. when the protecting group is t-butoxycarbonyl, and when the protecting group is phthalimido, removal is effected using an ethanolic solution of a hydrazine (using classical techniques) the latter being used when $R_2$ contains a fluoro atom. Removal of the isopropylidene protecting group of the ribofuranosyl moiety is easily effected by hydrolysis at room temperatures, (preferably using 1N sulfuric acid), generally simultaneously with the N-protecting groups. Isolation and purification of the intermediate and final products of reaction scheme A is effected by standard techniques, e.g., recrystallization, HPLC, flash chromatography (on silica gel) and the like.

The preparation of the intermediates required for the condensation of reaction scheme A, i.e., those intermediates defined for $R_2X'$, may be effected by the use of analogously known procedures such as those outlined in the below described generic processes which are illustrated in the below particularized examples.

In those instances wherein $R_2X'$ represents subgeneric group 3e, the reaction proceeds under A-a conditions wherein X' is preferably chloro and the N-protecting group is Boc, the appropriate V, W, Z-substituted-N-protected-4-chloro-2-butene-1-amine may conveniently be prepared by the following reaction scheme.

Reaction Scheme B

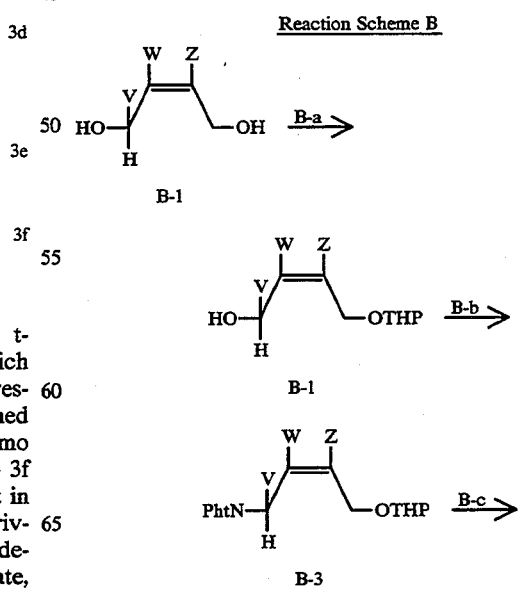

-continued
Reaction Scheme B

BocNH—V(H)—C(W)(Z)—OH  →(B-d)

B-4

BocNH—V(H)—C(W)(Z)—Cl

B-5 wherein the protecting groups (Pht and Boc) and V, W and Z are as previously defined and (THP) is tetrahydropyran.

In step B-a the diol is reacted with dihydropyran in the presence of catalytic quantities of pyridinium-p-toluene sulfonate at about 0° C. in an anhydrous solvent (or mixture) (e.g., $CH_2Cl_2$:THF; 2:1) for about 24–48 hours. Conversion of B-2 to B-3 is initiated by a Mitsunobu-type intermolecular dehydration reaction on treatment with diethylazodicarboxylate (DEAD) and triphenylphosphine under mild neutral conditions under an inert atmosphere (nitrogen) at about 0° C. in an anhydrous solvent (e.g., THF) in the presence of phthalimide; the reaction continuing at room temperature for about 12 hours.

The resulting B-3 products, upon treatment with hydrazine hydrate in ethanol at reflux for about 12 hours, to remove the phthalimido and THP protecting groups and the free amine is re-protected with di-t-butyldicarbonate by refluxing in dichloromethane. The alcohols (B-4) are converted to their chlorides by reaction with mesylchloride under basic conditions (TEA) in an anhydrous solvent, preferably dichloromethane. These cis products of Formula 3e, after purification, generally using flash chromatographic techniques on silica gel, are ready for condensation with the reactants of Formula 2, according to the techniques described for reaction scheme A.

In those instances wherein it is desired to prepare the trans-configuration of compounds of 3-e, it is preferred to utilize a W, Z-V-substituted N-protected trans-1-bromo-4-amino-2-butene, (i.e., 3-e), the reactants are readily prepared by reacting a V-W, Z-substituted trans-1-bromo-4-amino-2-butene with potassium phthalimide in anhydrous DMF at about 50° C. for 24 hours according to standard procedures well known in the art. The necessary $R_2X'$ reactants of the class 3-c are readily prepared from the appropriate W, Z, $V_2$-substituted $\alpha,\alpha$-dichloroxylene wherein the compound is subjected to a displacement reaction with potassium phthalimide to form an $\alpha$-phthalimido-$\alpha'$-chloroxylene by heating the reactants at about 50° C. for about 24 hours in anhydrous DMF and the so-formed compound is purified by the usual techniques of flash chromatography from silica gel. Starting from the appropriately V, W, Z-substituted 3-chloro-2-chloromethyl-1-propene the desired $R_2X'$ reactants of class 3-a may similarly be prepared by the foregoing described displacement reaction with potassium phthalimide by heating the reactants at about 50° C. for about 24 hours in anhydrous dimethylfluoromethane followed by purification with the usual techniques, e.g., flash chromatography. In those instances wherein the particular V, W, Z-substituted reactant is not a known compound, such compounds may be prepared by techniques and procedures well understood and known in the art.

In addition to the specific examples described below, chemistry for the preparation of cis-5'-(4-amino-4-carboxy-2-butenyl)methyladenosine may be analogously derived from Tolman and Sedmera's article (Tetrahedron Letters, Vol. 29, No. 47, pp. 6183–6184, 1988) "Unsaturated Amino Acids: Synthesis of Trans-3,4-Didehydro Analogues of L-Ornithine and L-Argine". The application of this chemistry is schematically represented by the following reaction scheme.

Reaction Scheme C $(MeO_2C)_2$—C(NHAc)—CH=CHCO$_2$t-Bu  →(a)

(6)

$(MeO_2C)_2$—C(NHAc)—C≡CCO$_2$t-Bu  →(b)

(7)

$(MeO_2C)_2$—C(NHAc)—C≡C—CH$_2$OH  →(c)

(8)

HOOC—CH(NHAc)—C≡C—CH$_2$OH  →(d)

(9)

Bu-tOOC—CH(NHAc)—C≡C—CH$_2$Cl  →(e)

(10)

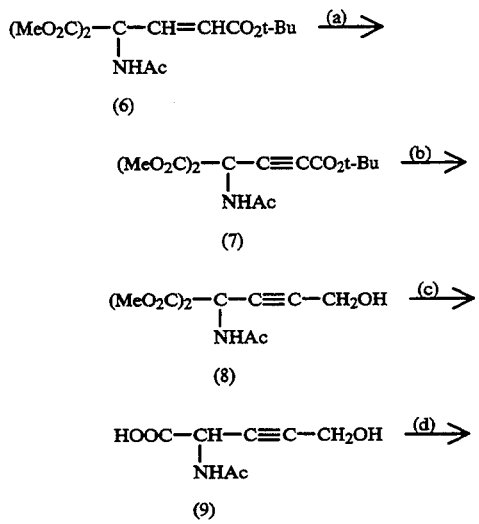

(11)

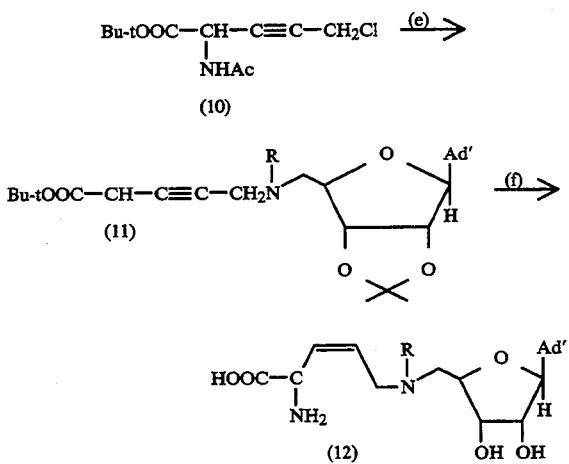

(12)

In effecting the foregoing reaction scheme step (a) involves the dibromination of (6) by reaction with bromine, said reaction being placed in a suitable solvent (e.g., $CCl_4$) at room temperature. The resulting dibromo analog is debrominated by reaction with potassium t-butoxide in tetrahydrofuran or with an amine such as DBU. The so-obtained compound (7) is sequentially treated with (1) trifluoroacetic acid at 25° C. for 20 minutes, (2) treated with thionyl chloride at 25° C. for 3 hours, and (3) treated with DiBal in tetrahydrofuran at −30° C. for 1 hour to produce compound (8). Step (c) involves the sequential treatment of (8) with a base (e.g., NaOH/H$_2$O in tetrahydrofuran for 20 minutes, followed by treatment with diluted HCl at 50° C. to produce compound (9). This compound is treated with isobutylene, in the presence of catalytic amounts of sulfuric acid and the resulting alcohol is converted to its corresponding chloride by treatment with mesyl chloride to produce compound (10). This compound is then subjected to reaction with the adenosine derivatives of formula (2) according to the procedure of Reaction Scheme A (wherein compound (10) corresponds to $R_2X'$ with $X'$ being chloro) to produce a compound analogously corresponding to compounds 4 [i.e., compound (11)].

The resulting triple-bond-containing compound is partially reduced using hydrogenation in the presence of a Lindlar catalyst ($H_2/PdSO_4$) and the resulting butene is treated with sulfuric acid (to remove the t-butoxide and isopropylidene protecting groups). The final step is to subject the so-produced penultimate compound to acylase I (Merck) at a pH of 7.2 at 37° C. to remove the N-protecting acyl moiety to produce a desired compound (12), e.g., cis-5'-deoxy-5'-(4-amino-4-carboxy-2-butene)methylaminoadenosine.

The following examples illustrate the preparation of the necessary intermediates and final products of this invention.

EXAMPLE 1

Preparation of
CIS-5'-DEOXY-5'(4-AMINO-2-BUTENYL)ME-THYLAMINOADENOSINE

Step A:
CIS-4-TETRAHYDROPYRANYLOXY-2-BUTENE-1-OL

Dihydropyran (9.1 ml, 100 mmol) was added dropwise to a cooled (0° C.) solution of 2-butene-1,4-diol (8.8 g, 10 mmol) and pyridinium paratoluenesulfonate (0.25 g, 10 mmol) in anhydrous dichloromethane:tetrahydrofuran (2:1). The mixture was stirred two days at 0° C. then concentrated in vacuo. The residue was purified by flash chromatography on silica gel (ethyl acetate:-hexane 3:7) to give 8.3 g of the title compound (49%).

Step B:
CIS-1-PHTHALIMIDO-4-TETRAHY-DROPYRANYLOXY-2-BUTENE

Under a nitrogen atmosphere diethylazodicarboxylate (1.6 ml, 10 mmol) was added to a cooled (0° C.) solution of cis-4-tetrahydropyranyloxy-2-butene-1-ol (1.7 g, 10 mmol), triphenyl phosphine (2.2 g, 10 mmol) and phthalimide (1.47 g, 10 mmol) in anhydrous tetrahydrofuran (50 ml). When the addition was completed (5 min) the reaction mixture was allowed to warm at room temperature and was stirred 12 h. Then the mixture was concentrated in vacuo, diluted with ethyl acetate (200 ml) and washed with brine (150 ml). After usual work-up (the aqueous phase was extracted three times with 100 ml portions of ethyl acetate), the organic phase was dried over magnesium sulfate, filtered and concentrated in vacuo) the product was purified by flash chromatography on silica gel (ethyl acetate:hexane; 2:8) to give 1.9 g of the title compound (64%).

Step C:
CIS-TERTIOBUTOXYCARBONYL-4-HYDROXY-2-BUTENYL-1-AMINE

A solution of cis-1-phthalimido-4-tetrahydropyranyloxy-2-butene (1.9 g, 6.3 mmol) and hydrazine hydrate (0.35 ml, 6.9 mmol) in ethanol (20 ml) was heated under reflux 12 hours. Then the mixture was concentrated in vacuo, diluted with 1N hydrochloric acid (20 ml) and heated under reflux for two hours. Then the phthalylhydrazide was filtered off and the filtrate was concentrated in vacuo. The residue was taken in dichloromethane (100 ml) neutralized with triethylamine (pH 8.9) and a solution of ditertiobutyldicarbonate (1.65 g, 7.5 mmol) in dichloromethane (5 ml) was added. The mixture was heated under reflux overnight and, after usual work-up, the product was obtained by flash chromatography on silica gel (ethyl acetate: hexane; 25:75) (0.8 g, 74%).

Step D:
CIS-N-TERTIOBUTOXYCARBONYL-4-CHLORO-2-BUTENYL-1-AMINE

Mesyl chloride (0.6 ml, 7.6 mmol) was added to a cooled (0° C.) solution of cis-tertiobutoxycarbonyl-4-hydroxy-2-butenyl-1-amine (1.3 g, 7 mmol) and triethylamine (1.1 ml, 7.6 mmol) in anhydrous dichloromethane (30 ml). The mixture was stirred overnight and, after usual work-up, the title product was purified by flash chromatography on silica gel (ethyl acetate: hexane; 2:8) (0.8 g, 57%).

Step E:
CIS-5'-DEOXY-5'(N-TERTIOBUTOXYCARBO-NYL-4-AMINO-2-BUTENYL)METHYL-AMINO-2',3'-ISOPROPYLIDENEADENOSINE A solution of cis-N-tertiobutoxycarbonyl-4-chloro-2-butenyl-1-amine (0.6 g, 3 mmol), 5'-deoxy-5'-methylamino-2',3'-isopropylideneadenosine (0.97 g, 3 mmol), potassium carbonate (0.42 g, 3 mmol) and sodium iodide (0.05 g, 0.3 mmol) in acetonitrile (20 ml) was heated under reflux overnight. Then the mixture was diluted with ethyl acetate, washed with brine and dried over magnesium sulphate. Then the product was purified by flash chromatography on silica gel (diethyl amine:chloroform; 2:98) (1.1 g, 55%).

Step F:
CIS-5'-DEOXY-5'(4-AMINO-2-BUTENYL)ME-THYLAMINOADENOSINE

A solution of cis-5'-deoxy-5'[(N-tertiobutoxycarbo-nyl-4-amino-2-butenyl)methyl-amino]-2',3'-iso-propylideneadenosine (0.9 g, 1.8 mmol) in 1N sulphuric acid (5 ml) was left two days at room temperature. Then the mixture was diluted with ethanol (200 ml) and cooled (0° C.) overnight. The precipitate was filtered off, dissolved in the minimum amount of water and then re-precipitated with ethanol (200 ml). This procedure was repeated twice to give the title compound (0.5 g), mp: 260° C. decomposed.

EXAMPLE II

Preparation of
TRANS-5'-DEOXY-5'-(4-AMINO-2-BUTENYL)METHYLAMINOADENOSINE

Step A:
TRANS-1-BROMO-4-PHTHALIMIDO-2-BUTENE

A mixture of trans-1,4-dibromo-2-butene (6.4 g, 30 mmol) and potassium phthalimide (5.6 g, 30 mmol) in anhydrous dimethyl formamide (200 ml) was heated at 50° C. for 24 h. Then the reaction mixture was concentrated in vacuo, dissolved in ethyl acetate, washed with brine and the pure title product was obtained by flash chromatography on silica gel (ethyl acetate: hexane; 15:85) (3.2 g, 40%).

Step B:

TRANS 5'-DEOXY-5'(4-PHTHALIMIDO-2-BUTENYL)METHYLAMINO-2',3'-ISOPROPYLIDENEADENOSINE

A mixture of trans-1-bromo-4-phthalimido-2-butene (2 g, 7.5 mmol), potassium carbonate (1.6 g, 11.5 mmol) and 5'-deoxy-5'-methylamino-2',3'-isopropylideneadenosine (2.4 g, 7.5 mmol) in anhydrous acetonitrile (100 ml) was heated under reflux overnight. Then the mixture was concentrated in vacuo, dissolved in dichloromethane, filtered and purified by flash chromatography on silica gel (chloroform: diethylamine; 98:2) to afford the title compound (1.25 g, 33%).

Step C:
TRANS-5'-DEOXY-5'-(4-TERTIOBUTOXYCARBONYLAMINO-3-BUTENYL)-METHYLAMINO-2',3'-ISOPROPYLIDENEADENOSINE A mixture of trans-5'-deoxy-5'-(4-phthalimido-2-butenyl)-methylamino-2',3'-isopropylideneadenosine (1 g, 2 mmol) and hydrazine hydrate (0.1 ml, 2 mmol) in absolute ethanol was heated under reflux overnight. Then the mixture was concentrated in vacuo, dissolved in water (30 ml) and the pH was adjusted to 4 with glacial acetic acid and cooled to 0° C. Then the mixture was filtered off and the filtrate neutralized with triethylamine to pH 9 and concentrated in vacuo. Then the residue was dissolved in dichloromethane, and ditertiobutyldicarbonate (0.45 g, 2 mmol) was added. The mixture was heated under reflux overnight and, after usual work-up, the product was purified by flash chromatography on silica gel (diethylamine:dichloromethane; 2:98) to give the title compound (0.5 g, 51%).

Step D:
TRANS-5'-DEOXY-5'-(4-AMINO-2-BUTENYL)-METHYLAMINOADENOSINE

A suspension of trans-5'-deoxy-5'-(4-tertiobutoxycarbonylamino-2-butenyl)methylamino-2',3'-isopropylideneadenosine (0.4 'g, 0.96 mmol) in 1N sulphuric acid (3 ml) was stirred 2 days at room temperature. Then the mixture was diluted with absolute ethanol (100 ml) and cooled at 0° C. overnight. The product was filtered off, dissolved in the minimum amount of water and precipitated with ethanol (100 ml). This procedure was repeated twice to afford the title compound (0.16 g). mp: 250°–260° C. decomposed.

EXAMPLE III

Preparation of
5'-DEOXY-5'-(4-AMINO-2-BUTYNYL)METHYLAMINOADENOSINE

Step A:
1-CHLORO-4-PHTHALIMIDO-2-BUTYNE

A mixture of 1,3-dichloro-2-butyne (4.9 ml, 50 mmol) and potassium phthalimide (5.6 g, 30 mmol) was heated at 50° C. during 24 h. Then the mixture was concentrated in vacuo, diluted with ethyl acetate and, after usual work-up, the product was purified by flash chromatography on silica gel to give 4.3 g of the title compound (62%).

Step B:
5'-DEOXY-5'-(4-PHTHALIMIDO-2-BUTYNYL)-METHYLAMINO-2',3'-ISOPROPYLIDENEADENOSINE A mixture of 1-chloro-4-phthalimido-2-butyne (1.4 g, 6 mmol), 5'-deoxy-5'-methylamino-2',3'-isopropylideneadenosine (1.6 g, 5 mmol) and sodium iodide (0.075 g, 0.5 mmol) in anhydrous acetonitrile (100 ml) was heated under reflux overnight. Then the mixture was concentrated, diluted with dichloromethane, filtered and purified by flash chromatography on silica gel (diethylamine:chloroform; 2:98) to give the title compound (1.6 g, 64%).

Step C:
5'-DEOXY-5'-(4-TERTIOBUTOXYCARBONYLAMINO-2-BUTYNYL)METHYLAMINO-2',3'-ISOPROPYLIDENEADENOSINE A mixture of 5'-deoxy-5'-(4-phthalimido-2-butynyl)-methylamino-2',3'-isopropylideneadenosine (1 g, 19 mmol) and methyl hydrazine (0.5 ml, 10 mmol) in absolute ethanol (3 ml) was heated under reflux overnight. Then the mixture was concentrated in vacuo, dissolved in a mixture of tetrahydrofuran:water (1:1, 200 ml), and a solution of ditertiobutyl dicarbonate (0.5 g, 2.5 mmol) in tetrahydrofuran (10 ml) was added. The pH of the mixture was adjusted to 9 with triethylamine and then the mixture was heated under reflux for 24 h. Then the reaction mixture was concentrated in vacuo, diluted with ethyl acetate and, after usual work-up, the product was obtained by flash chromatography on silica gel (diethylamine:chloroform; 2:98) (0.5 g, 56%).

Step D:
5'-DEOXY-5'-(4-AMINO-2-BUTYNYL)METHYLAMINOADENOSINE

A suspension of 5'-deoxy-5'-(4-tertiobutoxycarbonylamino-2-butynyl)methylamino-2', 3'-isopropylideneadenosine (0.4 g, 0.82 mmol) in 1N sulphuric acid (25 ml) was stirred 2 days at room temperature. Then the mixture was diluted with ethanol (100 ml;) and stirred at 0° C. overnight. The product was filtered off, dissolved in the minimum amount of water and diluted with ethanol (100 ml). This procedure was repeated twice to afford pure 5'-deoxy-5'-(4-amino-2-butynyl)methylaminoadenosine as white crystals (0.2 g). mp: 230°–240° C. decomposed. This compound, of course, can be reduced to form the corresponding cis double-bonded compound.

EXAMPLE IV

Preparation of
5'-DEOXY-5'-(ORTHO-AMINOMETHYL BENZYL)METHYLAMINOADENOSINE

Step A:
α-PHTHALIMIDO-α'-CHLOROXYLENE

A mixture of α,α'-dichloroxylene (8.75 g, 50 mmol) and potassium phthalimide (5.6 g, 30 mmol) was heated to 50° C. for 24 h. Then the reaction mixture was concentrated in vacuo, dissolved in ethyl acetate and, after usual work-up, the desired compound was obtained by flash chromatography on silica gel (ethyl acetate:hexane; 15:85) (6 g, 65%).

Step B:
5'-DEOXY-5'-(ORTHO-PHTHALIMIDOMETHYLBENZYL)METHYLAMINO-2',3-ISOPROPYLIDENEADENOSINE A mixture of α-phthalimido-α'-chloroxylene (1.6 g, 5.5 mmol), potassium carbonate (0.7 g, 5 mmol) sodium iodide (0.07 g, 0.5 mmol) and 5'-deoxy-5'-methylamino-2',3'-isopropylideneadenosine (1.5 g, 4.7 mmol) in anhydrous acetonitrile was heated under reflux overnight. Then the mixture was concentrated in vacuo, dissolved in dichloromethane, filtered and then purified by flash chromatography on silica gel (chloroform: diethylamine 98:2) to give the title compound (1.8 g, 67%).

Step C:
5'-DEOXY-5'-(ORTHO-TERTIOBUTOXYCARBONYLAMINOMETHYLBENZYL)ME-

THYLAMINO-2',3'-ISOPROPYLIDENEADENOSINE

A mixture of 5'-deoxy-5'-(ortho-phthalimido-methylbenzyl)methylamino-2',3'-isopropylideneadenosine (13 g, 2.3 mmol) and hydrazine hydrate (0.12 ml, 2.3 mmol) in absolute ethanol (100 ml) was heated under reflux overnight. Then the mixture was concentrated in vacuo, diluted in water (30 ml), and glacial acetic acid was added to adjust at pH 4 and left at 0° C. Then the mixture was filtered off and the filtrate was neutralized with triethylamine to adjust the pH of the reaction mixture around 9. Then the mixture was concentrated in vacuo, diluted with dichloromethane, and ditertiobutyldicarbonate (0.5 g, 2.3 mmol) was added. Then the mixture was heated under reflux overnight and, after usual work-up, the title compound (0.8 g, 67%) was isolated by flash chromatography on silica gel (chloroform: diethylamine; 98:2).

Step D:
5'-DEOXY-5'-(ORTHO-AMINOMETHYLBENZYL)METHYLAMINOADENOSINE

A suspension of 5'-deoxy-5'-(ortho-tertiobutoxycarbonylaminomethylbenzyl)methylamino-2',3'-isopropylideneadenosine (0.45 g, 0.83 mmol) in 1N sulphuric acid (25 ml) was stirred two days at room temperature. Then the mixture was diluted with ethanol (100 ml) and stored at 0° C. overnight. The precipitate was filtered off, dissolved in the minimum amount of water and reprecipitated with ethanol (100 ml). This procedure was repeated twice to give the title compound (0.4 g). mp: 230°–240° C. decomposed.

EXAMPLE V

5'-DEOXY-5'-(3-AMINO-2-METHYLENEPROPYL)METHYLAMINOADENOSINE

Step A:
1-PHTHALIMIDO-3-CHLORO-2-METHYLENEPROPANE

A mixture of 3-chloro-2-chloromethyl-1-propene (6.55 g, 50 mmol) and potassium phthalimide (5.6 g, 30 mmol) in anhydrous dimethylformamide (200 ml) was heated two days at 50° C. Then the mixture was concentrated in vacuo and, after usual work-up, the product was purified by flash chromatography on silica gel (ethyl acetate:hexane; 15:85) (4.2 g, 78%).

Step B:
5'-DEOXY-5'-(3-PHTHALIMIDO-2-METHYLENEPROPYL)METHYLAMINO-2',3'-ISOPROPYLIDENEADENOSINE A mixture of 1-phthalimido-3-chloro-2-methylenepropane (0.87 g, 5 mmol), potassium carbonate (0.7 g, 5 mmol), sodium iodide (0.08 g, 0.5 mmol) and 5'-deoxy-5'-methylamino-2',3'-isopropylideneadenosine (1.6 g, 5 mmol) in anhydrous acetonitrile (100 ml) was heated two days under reflux. Then the mixture was concentrated in vacuo, diluted with dichloromethane, filtered and the product was purified by flash chromatography on silica gel (diethyl amine:chloroform; 2:98) to give 2.85 g (78%) of the title compound.

Step C:
5'-DEOXY-5'-(3-TERTIOBUTOXYCARBONYLAMINO-2-METHYLENEPROPYL)METHYLAMINO-2',3'-ISOPROPYLIDENEADENOSINE A mixture of 5'-deoxy-5'-(3-phthalimido-2-methylenepropyl)methylamino-2',3'-isopropylideneadenosine (2.3 g, 4.4 mmol), methyl hydrazine (1.5 ml, 30 mmol) in absolute ethanol (5 ml) was heated two days under reflux. Then the mixture was concentrated in vacuo, dissolved in chloroform (5 ml), the pH was adjusted around 9 with triethylamine and then a solution of ditertiobutyl dicarbonate (8.8g, 4.4 mmol) in chloroform (5 ml) was added. The resulting mixture was heated overnight under reflux and, after usual work-up, the product was purified by flash chromatography on silica gel (diethylamine: chloroform; 2:98) to give 1.25 g (64%) of the title compound.

Step D:
5'-DEOXY-5'-(3-AMINO-2-METHYLENEPROPYL)METHYLAMINOADENOSINE

A suspension of 5'-deoxy-5'-(3-tertiobutoxycarbonylamino-2-methylenepropyl)methylamino-2',3'-isopropylideneadenosine (0.65 g, 1.3 mmol) in 1N sulphuric acid (4 ml) was stirred two days at room temperature. Then the mixture was diluted with absolute ethanol (150 ml) and left at 0° C. overnight. The precipitate was filtered off, dissolved in a minimum amount of water and diluted with absolute ethanol (150 ml). This procedure was repeated twice to afford the title compound as white crystals (0.55 g, mp: 230°–240° C. decomposed).

EXAMPLE VI

Preparation of
5'-DEOXY-5'-(4-AMINO-2,2-DIFLUOROBUTYL)-METHYLAMINOADENOSINE

Step A:
4-PHTHALIMIDO-2,2-DIFLUOROBUTYL-TRIFLUOROMETHANESULFONATE

Triflic anhydride (1.1 ml, 6.6 mmol) was added to a cooled (0° C.) solution of 4-phthalimido-2,2-difluoro-1-butanol (1.53 g, 6 mmol), pyridine (0.53 ml, 6.6 mmol) in anhydrous dichloromethane (50 ml). The mixture was stirred 1 h at 0° C. and, after usual work-up, the product was purified by flash chromatography on silica gel (ethyl acetate:hexane; 20:80) to give 1.8 g (78%) of the title compound.

Step B:
5'-DEOXY-5'-(4-PHTHALIMIDO-2,2-DIFLUOROBUTYL)METHYLAMINO-2',3'-ISOPROPYLIDENEADENOSINE A mixture of 4-phthalimido-2,2-difluorobutyl-trifluoromethanesulfonate (1.8 g, 4.6 mmol), 5'-deoxy-5'-methylamino-2',3'-isopropylideneadenosine (1.3 g, 4.3 mmol) and triethylamine (0.6 ml, 4.3 mmol) in anhydrous dimethylformamide was heated two days at 50° C. Then the mixture was concentrated in vacuo and the product was purified by flash chromatography on silica gel (diethylamine:chloroform; 2:98) (1.7 g, 70%).

Step C:
5'-DEOXY-5'-(4-TERTIOBUTOXYCARBONYLAMINO-2,2-DIFLUOROBUTYL)METHYLAMINO-2',3'-ISOPROPYLIDENEADENOSINE A mixture of 5'-deoxy-5'-(4-phthalimido-2,2-difluorobutyl)methylamino-2',3'-isopropylideneadenosine (15 g, 2.7 mmol) and hydrazine hydrate (0.135 g, 2.7 mmol) in ethanol (20 ml) was heated under reflux overnight. Then the mixture was concentrated in vacuo, diluted with water, and glacial acetic acid was added until the pH was adjusted to 4. The mixture was left at 0° C. and then filtered off. The filtrate was neutralized to pH 9 with triethylamine, concentrated in vacuo, diluted with dichloromethane and then ditertiobutyldicarbonate (0.6 g, 2.7 mmol) was added. The mixture was heated under reflux overnight and, after usual work-up, the product was purified by flash chromatography on silica gel (diethylamine: chloroform; 2:98) to give 1.1 g (75%) of the title compound.

Step D:
5'-DEOXY-5'-(4-AMINO-2,2-DIFLUOROBUTYL)METHYLAMINOADENOSINE

A suspension of 5'-deoxy-5'-(4-tertiobutoxycarbonylamino-2,2-difluorobutyl)methylamino-2',3'-isopropylideneadenosine 1N sulphuric acid (4.5 ml) was stirred two days at room temperature. Then the mixture was diluted with ethanol (100 ml) and left overnight at 0° C. The precipitate was filtered off, dissolved in a minimum amount of water and precipitated with ethanol (150 ml). This procedure was repeated twice to afford the title compound (0.5 g, 60%) as white crystals (mp: 240° C. decomposed).

EXAMPLE VII

Preparation of
CIS-5'-DEOXY-5'-(4-AMINO-2-FLUORO-2-BUTENYL)METHYLAMINOADENOSINE

Step A:
CIS-4-PHTHALIMIDO-2-FLUORO-1-TETRAHYDROPYRANYL-2-BUTENE

A mixture of cis-4-chloro-2-fluoro-1-tetrahydropyranyl-2-butene (6.3 g, 30 mmol) and potassium phthalimide (5.6 g, 30 mmol) in anhydrous dimethyl formamide (200 ml) was heated at 50° C. for 24 h. Then the reaction mixture was concentrated in vacuo, dissolved in ethyl acetate, washed with brine and the pure title compound cis-4-phthalimido-2-fluoro-2-tetrahydropyranyl-2-butene (6 g, 70%) was obtained by flash chromatography on silica gel (ethyl acetate:hexane; 2:8).

Step B:
CIS-N-TERTIOBUTOXYCARBONYL-2-FLUORO-4-HYDROXY-2-BUTENYL-1-AMINE

A solution of cis-4-phthalimido-2-fluoro-2-tetrahydropyranyl-2-butene (5.7 g, 20 mmol) and hydrazine hydrate (1.1 ml, 22 mmol) in ethanol (30 ml) was heated under reflux for 12 h. Then the mixture was concentrated in vacuo, diluted with 1N HCl (20 ml) and heated under reflux for 2 h. Then the phthalhydrazide was filtered off and the filtrate was concentrated in vacuo. The residue was taken up in dichloromethane (150 ml), neutralized with triethylamine until pH 9, and a solution of ditertiobutyldicarbonate (5 g, 22 mmol) in dichloromethane (10 ml) was added. The mixture was heated under reflux overnight and, after usual work-up, the product was obtained by flash chromatography on silica gel (ethyl acetate:hexane; 25:75) (3 g, 75%).

Step C:
CIS-N-TERTIOBUTOXYCARBONYL-2-FLUORO-4-CHLORO-2-BUTENYL-1-AMINE

Mesylchloride (0.9 ml,, 11 mmol) was added to a cold (0° C.) solution of cis-N-tertiobutoxycarbonyl-2-fluoro-4-hydroxy-3-butenyl-1-amine (2.05 g, 10 mmol) and triethylamine (1.6 ml, 11 mmol) in anhydrous dichloromethane (40 ml). The mixture was stirred overnight and, after usual work-up, the title compound cis-N-tertiobutoxycarbonyl-2-fluoro-4-chloro-2-butenyl-1-amine was obtained by flash chromatography on silica gel (ethyl acetate:hexane; 15:85) (1.7 g, 75%).

Step D:
CIS-5'-DEOXY-5'-(4-TERTIOBUTOXYCARBONYLAMINO-2-FLUORO-2-BUTENYL)METHYLAMINO-2',3'-ISOPROPYLIDENEADENOSINE A solution of 5'-deoxy-5'-methylamino-2',3'-isopropylideneadenosine (1.65 g, 5 mmol), cis-N-tertiobutoxycarbonyl-2-fluoro-4-chloro-2-butenyl-1-amine (1.2 g, 4 mmol), potassium carbonate (0.7 g, 4 mmol) and sodium iodide (0.07 g, 0.5 mmol) in anhydrous acetonitrile (30 ml) was heated under reflux overnight. The mixture was concentrated in vacuo, diluted with ethyl acetate, washed with brine and dried over MgSO4. The product was purified by flash chromatography on silica gel (diethylamine: chloroform; 2:98) (1.7 g, 70%).

Step E:
CIS-5'-DEOXY-5'-(4-AMINO-2-FLUORO-2-BUTENYL)METHYLAMINOADENOSINE

A suspension of cis-5 "-deoxy-5'-(4-tertiobutoxycarbonylamino-2-fluoro-2-butenyl )methylamino-2',3'-isopropylideneadenosine in 1N sulphuric acid (5 ml) was stirred for 2 days at room temperature. Then the mixture was diluted with absolute ethanol (200 ml) and kept at 0° C. overnight. The precipitate was collected, dissolved in a minimum of water, and reprecipitated with absolute ethanol (200 ml). This procedure was repeated twice to give the title compound cis-5'-deoxy-5'-(4-amino-2-fluoro-2-butenyl)methylaminoadenosine (1 g, 75%; mp: 250°–260° C. decomposed).

EXAMPLE VIII

Preparation of
5'-DEOXY-5'-(3-AMINO-2,2-DIFLUOROPROPYL)-METHYLAMINOADENOSINE

Step A:
ETHYL 2,2-DIFLUORO-3-HYDROXYPROPIONATE

A mixture of paraformaldehyde (4.5 g, 50 mmol), ethyl difluorobromoacetate (10.2 g, 50 mmol) and activated zinc dust (3.3 g, 40 mmol) in anhydrous tetrahydrofuran was heated under reflux for 0.5 h. Then the mixture was treated with a saturated aqueous solution of ammonium chloride and extracted with diethyl ether. After usual work-up the desired compound ethyl 2,2-difluoro-3-hydroxypropionate was obtained by flash chromatography on silica gel (ethyl acetate:hexane; 25:75) (4.1 g, 53%).

Step B:
ETHYL 2,2-DIFLUORO-3-TETRAHYDROPYRANYLOXYPROPIONATE

Dihydropyrane (2 ml, 22 mmol) was added to a solution of ethyl 2,2-difluoro-3-hydroxypropionate (3.1 g, 20 mmol) and pyridinium p-toluene sulfonate (0.25 g, 1 mmol) in anhydrous dichloromethane (50 ml). The mixture was stirred overnight at room temperature and the desired compound ethyl 2,2-difluoro-3-tetrahydropyranyloxypropionate was obtained by flash chromatography on silica gel (ethyl acetate:hexane; 15:85) (4 g, 80%).

Step C:
2,2-DIFLUORO-3-TETRAHYDROPYRANYLOXY-1-PROPANOL

A solution of ethyl 2,2-difluoro-3-tetrahydropyranyloxypropionate (3.5 g, 15 mmol) in absolute ethanol (10 ml) was added dropwise to a slurry of sodium borohydride (0.57 g, 15 mmol) at room temperature in absolute ethanol (20 ml). Then the mixture was stirred an additional hour at room temperature. Then the mixture was concentrated in vacuo, hydrolyzed with aqueous ammonium chloride, extracted with ethyl acetate and dried over magnesium sulfate. The product was purified by flash chromatography on silica gel (ethyl acetate:hexane; 25:75) (2.7 g, 90%).

Step D:
2,2-DIFLUORO-3-TETRAHYDROPYRANYLOXYPROPYL TRIFLUOROMETHANESULFONATE

Triflic anhydride (1.8 ml, 11 mmol) was added to a cold (0° C.) solution of 2,2-difluoro-3-tetrahydropyranyloxy-1-propanol 91.6 g, 10 mmol), pyridine (0.9 ml, 11 mmol) in anhydrous dichloromethane (50 ml). The mixture was stirred 1 h at 0° C. and, after usual work-up, the product was purified by flash chromatography on silica gel (ethyl acetate:hexane; 15:85) (2.6 g, 80%).

Step E:
2,2-DIFLUORO-3-PHTHALIMIDO-1-TETRAHYDROPYRANYLOXYPROPANE

A mixture of 2,2-difluoro-3-tetrahydropyranyloxypropyl trifluoromethanesulfonate (2.3 g, 7 mmol), potassium phthalimide (1.4 g, 7.7 mmol) and anhydrous dimethylformamide (50 ml) under nitrogen was stirred and heated at 85° C. overnight. After cooling, salts are filtered off, and the solvent was removed in uacuo. The residue was taken up in dichloromethane (100 ml), washed with 0.5M NaOH (30 ml) and brine. The organic phase was separated, dried over magnesium sulfate and concentrated. The desired compound 2,2-difluoro-3-phthalimido-1-tetrahydropyranyloxypropane was purified by flash chromatography on silica gel (ethyl acetate:hexane; 20:80) (2 g, 90%).

Step F:
2,2-DIFLUORO-3-PHTHALIMIDO-1-PROPANOL

A solution of 2,2-difluoro-3-phthalimido-1-tetrahydropyranyloxypropane (2 g, 6.15 mmol), paratoluene sulfonic acid (0.1 g) in absolute ethanol was stirred overnight at room temperature. Then the mixture was concentrated in vacuo, diluted with ethyl acetate and ., washed with brine. The organic phase was separated, dried over magnesium sulfate and concentrated in vacuo. The crude alcohol 2,2-difluoro-3-phthalimido-1-propanol (1.4 g) was used for the next step without further purification.

Step G:
2,2-DIFLUORO-3-PHTHALIMIDO-PROPYL TRIFLUOROMETHANE SULFONATE

Triflic anhydride (1.1 ml, 6.6 mmol) was added to a cold (0° C.) solution of 2,2-difluoro-3-phthalimido-1-propanol (1.4 g, 6 mmol), pyridine (0.5 ml, 6.6 mmol) in anhydrous dichloromethane (30 ml). The mixture was stirred 1 h at 0° C. and, after usual work-up, the product was purified by flash chromatography on silica gel (ethyl acetate:hexane; 20:80) (1.7 g, 75%).

Step H:
5'-DEOXY-5'-(2,2-DIFLUORO-3-PHTHALIMIDO-PROPYL)METHYLAMINO-2',3'-ISOPROPYLIDENEADENOSINE A mixture of 2,2-difluoro-3-phthalimido-propyl trifluoromethane sulfonate (1.5 g, 4 mmol), 5'-deoxy-5'-methylamino-2',3'-isopropylideneadenosine (1.2 g, 4.2 mmol) and triethylamine (0.55 ml, 4.2 mmol) in anhydrous dimethyl formamide was heated 2 days at 50° C. Then the mixture was concentrated in vacuo and the product was purified by flash chromatography on silica gel (diethylamine:chloroform; 2:98) (1.5 g, 75%).

Step I:
5'-DEOXY-5'-(2,2-DIFLUORO-3-TERTIOBUTOXYCARBONYLAMINOPROPYL)METHYLAMINO-2',3'-ISOPROPYLIDENEADENOSINE A mixture of 5'deoxy-5'-(2,2-difluoro-3-phthalimidopropyl)methylamino-2',3'-isopropylideneadenosine (1.1 g, 2 mmol) in ethanol (10 ml) was heated under reflux overnight. Then the mixture was concentrated in vacuo, diluted with 1N acetic acid until pH 4 was reached, and cooled at 0° C. The precipitate was filtered off and the filtrate was neutralized until pH 9 with triethylamine and concentrated in vacuo. The residue was taken up in dichloromethane and ditertiobutyldicarbonate (0.45 g, 2 mmol) was added. The mixture was heated under reflux overnight and, after usual work-up, the product was purified by flash chromatography on silica gel (diethylamine:chloroform; 2:98) (0.8 g, 70%).

Step J:
5'-DEOXY-5'-(3-AMINO-2,2-DIFLUOROPROPYL)METHYLAMINOADENOSINE

A suspension of 5'-deoxy-5'-(2,2-difluoro-3-tertiobutoxycarbonylaminopropyl)methylamino-2',3'-isopropylideneadenosine (0.8 g, 1.5 mmol) in 1N sulphuric acid (4 ml) was stirred 2 days at room temperature. Then the mixture was diluted with absolute ethanol (150 ml) and kept at 0° C. overnight. The precipitate was collected, dissolved in a minimum of water, and reprecipitated with absolute ethanol (150 ml). This procedure was repeated twice to give the title compound 5'-deoxy-5'-(3-amino-2,2-difluoropropyl)methylaminoadenosine (0.6 g, 80%: mp: 250°–260° C. decomposed).

EXAMPLE IX

Preparation of
CIS-5'-DEOXY-5'-(4-CARBOXY-4-AMINO-2-BUTENYL)METHYLAMINOADENOSINE Step A:
2-AMINO-5-HYDROXY-3-PENTYNOIC ACID A mixture of glyoxylic acid monohydrate (23 g, 250 mmol), propargyl alcohol (16.8 g, 300 mmol ), copper (II) chloride (3.2 g, 25 mmol) and ammonium acetate (49 g, 600 mmol) in ethanol (100 ml) is heated under reflux for 6 h. Then the reaction mixture is concentrated in vacuo, diluted with water (50 ml), acidified to pH 5 with 1N HCl and washed twice with ether (100 ml). Then the aqueous solution is poured on an ion exchange resin column (DOWEX 50, H+) The column is eluted with 1M ammonium hydroxide to give the title compound 2-amino-5-hydroxy-3-pentynoic acid.

Step B:
TERTIOBUTYL-2-AMINO-5-HYDROXY-B-PENTYNOATE

A suspension of 2-amino-5-hydroxy-3-pentynoic acid (12.5 g, 100 mmol) concentrated in sulphuric acid (2 ml) and isopropylene (50 ml) in a sealed Parr's flask is shaken 2 days at room temperature. The crude product, after evaporation of the excess of isopropylene, is used for the next step without further purification.

Step C:
TERTIOBUTYL-2-TERTIOBUTOXYCARBONYLAMINO-5-HYDROXY-3-PENTYNOATE

A solution of the crude tertiobutyl-2-amino-5-hydroxy-3-pentynoate (100 mmol), ditertiobutyldicarbonate (22 g, 100 mmol) and triethylamine (25 ml, 200 mmol) in chloroform is heated under reflux overnight. Then, after usual work-up, the product is purified by flash chromatography on silica gel (ethyl acetate:hexane; 20:80).

Step D:
CIS-TERTIOBUTYL-2-TERTIOBUTOXYCARBONYLAMINO-5-HYDROXY-3-PENTENOATE

A solution of tertiobutyl-2-tertiobutoxycarbonylamino-5-hydroxy-3-pentynoate (13.6 g, 50 mmol) in ethanol (200 ml) is hydrogenated in presence of Lindlar catalyst (0.6 g) at atmospheric pressure and room temperature. In 3 h one equivalent of hydrogen (1.1 liters) is taken up. Then the catalyst is removed by filtration and the mixture is concentrated in vacuo which will yield a clear oil. The title compound is obtained by flash chromatography on silica gel (ethyl acetate:hexane; 15:85.

Step E:
CIS-TERTIOBUTYL-2-TERTIOBUTOXYCARBONYLAMINO-5-CHLORO-3-PENTENOATE

Mesyl chloride (0.9 ml, 11 mmol) is added to a cold (0° C.) solution of cis-tertiobutyl-2-tertiobutoxycarbonylamino-5-hydroxy-3-pentenoate (2.75 g, 10 mmol) and triethylamine (1.6 ml, 11 mmol) in anhydrous dichloromethane (50 ml). The mixture is stirred overnight and, after usual work-up, the title compound is purified by flash chromatography on silica gel (ethyl acetate:hexane; 20:80).

Step F:
CIS-5′-DEOXY-5′-(4-TERTIOBUTOXYCARBONYL-3-TERTIOBUTOXYCARBONYLAMINO-2-BUTENYL)METHYLAMINO-2′,3′-ISOPROPYLIDENEADENOSINE A solution of cis-tertiobutyl-2-tertiobutoxycarbonylamino-5-chloro-3-pentenoate (1.5 g, 5 mmol), 5′-deoxy-5′-methylamino-2′,3′-isopropylideneadenosine (16 g, 5 mmol), potassium carbonate (0.7 g, 5 mmol) and sodium iodide (0.8 g, 0.5 mol) in acetonitrile (30 ml) is heated under reflux overnight. After usual work-up, the product is purified by flash chromatography on silica gel (diethylamine:chloroform; 2:98).

Step G:
CIS-5′-DEOXY-5′-(4-CARBOXY-4-AMINO-2-BUTENYL)METHYLAMINOADENOSINE

A suspension of cis-5′-deoxy-5′-(4-tertiobutoxycarbonyl-3-tertiobutoxycarbonylamino-2-butenyl )methylamino-2′-3′-propropylideneadenosine (1.5 g, 3 mmol) in 1N sulphuric acid (5 ml) is stirred 2 days at room temperature. Then the mixture is diluted with ethanol (200 ml) and kept at 0° C. overnight. The precipitate is collected, dissolved in a minimum amount of water, and reprecipitated with ethanol (200 ml). This procedure is repeated twice and will yield the title compound cis-5′-deoxy-5′-(4-carboxy-4-amino-2-butenyl)-methylaminoadenosine.

(Usual work-up involves the extraction of the product from the aqueous phase by three extractions with the organic solvent (as in Step C, Example I) and the organic phase dried over magnesium sulfate, filtered off and concentrated in vacuo).

The compounds of Formula I are inhibitors of decarboxylase enzymes which are involved in polyamine formation and therefore such compounds are useful as pharmacological agents. In particular, the compounds of Formula I are potent and irreversible inhibitors of S-adenosylmethionine decarboxylase (Ado Met DC) and therefore significantly interfere with the formation of spermine and spermidine and thus are useful adducts in the armentarium of researchers and clinicians in the study of polyamine formation and in the treatment of conditions and diseases related to the rapid proliferation of cell growth. Of particular importance is the use of the compounds of this invention in conjunction with known ornithine decarboxylase inhibitors, known antitumoral agents and with immunomodulators known for their use in diseases associated with the rapid proliferation of normal and transformed cells.

As is well known in the art, polyamines are associated with both normal and rapid proliferation of cells and, as is also well known, the levels of polyamines are high in embryonic systems, the testes and patients suffering from diseases associated with rapid proliferation of cell growth. It is also known that there is a correlation between the activity of the decarboxylase enzymes of ornithine, S-adenosylmethionine, arginine and lysine and polyamine formation. Thus with this interrelationship the compounds of this invention, by their unique ability to inhibit S-adenosylmethionine decarboxylase, are also useful to study the biochemical and pharmacological consequences of polyamine biosynthesis blockade in mammals, plants, bacteria and protozoa.

More specifically, some of the more promising end-use applications of the compounds, of this invention are the following applications.

The use of an Ado Met DC inhibitor of this invention, alone but more effectively in conjunction with an ornithine decarboxylase (ODC) inhibitor in mammals as postcoital contraceptives, inducers of menstruation, and as first-trimester abortifacients is clear for such use does not surgically invade the cavity of the uterus, does not require hospitalization, and can be administered with the minimum of medical supervision.

In addition to the foregoing, the compounds of this invention may be used to treat diseases which are caused by infections with animal parasites, particularly parasitic protozoa and parasitic nematodes. In the treatment of diseases caused by these parasites, the compounds of this invention may be used alone, or in combination with ornithine decarboxylase inhibitors and/or in combination with other agents known to be useful in the treatment of such diseases. In some instances, such as in treating Chagas Disease, it is preferred to utilize arginine decarboxylase inhibitors in conjunction with the compounds of this invention. Of particular interest is the treatment of African trypanosomiasis, Chagas Disease and *Pneumocystis carinii* pneumonia (PCP) in patients suffering from AIDS (particularly in conjunction with an ODC inhibitor), cryptosporidiosis and malaria.

Still more specifically, the compounds of this invention are particularly useful in treating:

(1) diseases caused by *Onchocerca Volvulus*, a filarial nematode living in subcutaneous tissue causing skin lesions and eye lesions (river blindness). These diseases are commonly treated with diethylcarbamazine which kills the microfilariae, but not the adult worms;

(2) diseases caused by *Wuchereria bancrofti*, a thread-like nematode the adults of which live in thin lymphatic vessels and which cause lymphangitis, dermatitis and cellulitis. These diseases are commonly treated with diethylcarbamazine but this treatment is known to be inadequate;

(3) diseases caused by *Loa loa*, a filarial worm causing Loaiasis characterized by hot erythematous Galabar swelling on extremities and periorbital tissues which also have been treated with diethylcarbamazine;

(4) diseases caused by *Trichomonas vaginalis* a sexually transmitted flagellate protozoa causing trichomoniasis which is commonly treated with metronidazole;

(5) diseases caused by *Giardia lamblia*, a flagellated protozoan parasite causing giardiasis in domestic dogs and wild animals as well as man, for which the drugs of choice are quinacrine hydrochloride and metronidazole;

(6) diseases caused by *Toxoplasma gondii*, a protozoan parasite of the sub-class coccidia causing congenital toxoplasmosis which may be treated with pyrimethamine and sulfadiazine;

(7) diseases caused by the malarias of the genus Plasmodium, e.g., *Plasmodium falciparum, Plasmodium vivax, Plasmodium ovale* and *Plasmodium malariae* which are the causes of malaria; the usual treatment is with chloriquine, quinine sulfate, pyrimethanine and sulfadiazine. In the treatment of this disease it is better to utilize the compounds of this invention in conjunctive therapy with the foregoing or with ODC inhibitors;

(8) diseases caused by *Trypanosoma cruzi*, a protozoa causing Chagas Disease, a disease which has a history of being difficult to treat. In the treatment of this disease with the compounds of this invention it is recommended that they be used in conjunctive therapy with arginine and agmatine decarboxylase inhibitors;

(9) diseases caused by the African trypanosomes, *Trypanosoma brucei gambiense* and *Trypanosoma brucei rhodesiense*, two subspecies of hemofiagellates which are responsible for African Trypanosomiasis, a disease treated by suramin and more recently by eflornithine. Of particular use in the treatment of this disease are the specific compounds cis-5'-deoxy-5'(4-amino-2-butenyl)methylaminoadenosine and cis-5'-deoxy-5'(4-carboxy-4-amino-2-butenyl)methylaminoadenosine.

(10) diseases caused by *Leishmania tropica* and *Leishmania mexicana* which are responsible for outaneous leishmaniasis, and visceral leishmaniasis (also called kala azar or black fever) which is caused by *Leishmania donovani*.

Furthermore, an Ado Met DC inhibitor of this invention may be used (alone or in combination with ODC inhibitors) as anti-infective agents being effective in the control of bacteria, fungi and viruses which are dependent upon polyamines for growth, for example *E. coli, Enterobacter, H. influenzae, Mycobacteria* species, *Staphylococcus aureus, Klebsiella*, viruses such as poxviruses, Herpes viruses, picornaviruses and influenza viruses. In the use of the compounds of this invention it is preferred to use such ODC inhibitors as α-difluoromethylornithine, α-monofluoromethylornithine, α-ethylnylornithine, (ε)-2-(fluoromethyl)dehydroornithine (and the methyl, ethyl and other esters thereof), and (2R,5R)-6-heptyne-2,5-diamine; said compounds and their uses being adequately described as to their preparation, their ODC inhibitory properties and to their end-use applications (see Inhibition of Polyamine Metabolism, (1987) edited by McCann, P. P., Pegg, A. E., and Sjoerdsma, A.).

The S-adenosylmethionine decarboxylase inhibitory properties of the compounds of Formula I may readily be determined by standard laboratory procedures well known in the art. For example, cis-5'-deoxy-5'-(4-amino-2-butenyl)methylaminoadenosine produces inactivation of rat liver Ado Met DC in vitro with a $t\frac{1}{2}=16$ minutes at 0.1 μM, a $t\frac{1}{2}=1.6$ minutes at 1 μM and a $t\frac{1}{2}=0.8$ minutes at 2 μM.

Illustrative of the effects of a compound of this invention (i.e., cis-5'-deoxy-5'-(4-amino-2-butenyl)methylaminoadenosine, identified below as MDL Compound) for the treatment of African Trypanosomiasis is an assay using *Trypanosoma brucei*-infected mice, as follows:

| Treatment of *Trypanosoma Brucei*-infected mice with MDL Compound | | | |
|---|---|---|---|
| Treatment | Dose | Days of Survival (a) | Mice cured/Total |
| None | — | 4, 4, 4, 4, 5 | — |
| MDL Compound | 10 (b) | 14, 15, 21 | 2/5 |
|  | 20 | 9, 13 | 3/5 |
|  | 50 | 12 | 4/5 |
| Eflornithine | 2% (c) | 21, 21 | 3/5 |

(a) includes those animals that died.
(b) MDL Compound was given intraperitoneally three times per day (8:30 a.m., 12:30 p.m. and 4:30 p.m.) for three consecutive days.
(c) Eflornithine was given in drinking water for three days.

Mice (20–22 g, CD-1, males) were infected with $2.5 \times 10^5$ *T. brucei* (EATRO 110) by intraperitoneal injection. Drug treatment commenced 24 h after infection. Mice surviving for 30 days after all controls were dead were considered cured. This method for drug testing is that of Bacchi et al. (1980) Science 210: 332–334, and successfully predicted the utility of eflornithine in human trypanosomiasis.

As pharmacologically useful agents the compounds of Formula I can be administered in various manners to the patient being treated to achieve the desired effect. The compounds can be administered alone or in combination with another according to standard techniques for conjunctive therapy, bearing in mind that the compounds of this invention preferably enhance established protocols when used to treat neoplasms. The compounds are preferably administered in the form of a pharmaceutical preparation. In general, the compounds may be administered orally, parenterally, for example, intravenously, intraperitoneally, or subcutaneously, infusionally or topically, as determined by factors well-known and appreciated by the skilled artisan. The amount of compound administered will vary over a wide range and can be any effective amount, depending on the patient to be treated, the condition being treated and the mode of administration. The effective amount of compound administered will vary from about 0.2 mg/kg to 200 mg/kg of body weight of the patient per treatment dose and preferably will be about 1 mg/kg to about 50 mg/kg of body weight of the patient per treatment dose.

The solid unit dosage forms can be of the conventional type. Thus, the solid form can be a capsule which can be of the ordinary gelatin type containing a novel compound of this invention and a carrier, for example, lubricant and inert fillers, such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredients can be compressed into pellets or small cylinders and implanted subcutaneously or intramuscularly as depot injections or implants. Implants may employ inert materials such as biodegradable polymers or synthetic silicones, for example, SILASTIC, silicone rubber manufactured by the Dow-Corning Corporation.

As is true for most generic classes of compounds suitable for pharmaceutical end-use applications, certain sub-classes and certain specific compounds are preferred. For the compounds of this invention (I) those compounds wherein R is hydrogen or methyl are preferred and those compounds wherein Q represents formulae Ie, particularly the cis-configuration, and those of Ia and Ic. Preferred specific compounds are cis-5'-deoxy-(4-amino-2-butenyl)methylamino adenosine, cis-5'-deoxy-(4-amino-2-butenyl)amino adenosine and their 2-fluoro, 3-fluoro, and 2,3-difluoro analogs, and 5'-deoxy-5'-(3-amino-2-methylenepropyl)methylaminoadenosine, 5'-deoxy-5'-(3-amino-2-methylenepropyl)aminoadenosine and the mono and difluoro analogs (X and/or Y of Ia are fluoro) thereof, and cis-5'-deoxy-5'-(4-amino-4-carboxy-2-butenyl)methylaminoadenosine and cis-5'-deoxy-5'-(4-amino-4'-carboxy-2-butenyl)aminoadenosine.

We claim:

1. A compound of the formula

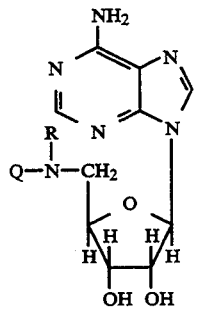

and the pharmaceutically acceptable salts thereof wherein

R represents H or a $C_{1-7}$ alkyl,

Q represents the moiety of the formula

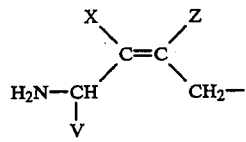

wherein

V represents H or —COOH,

X represents H, F, Cl, or Br, and

Z represents H, F, Cl, or Br.

2. A compound of claim 1 wherein R is methyl or H.

3. A compound of claim 1, said compound being cis-5'-deoxy-5'-(4-amino-2-butenyl)ethylaminoadenosine.

4. A compound of claim 1, said compound being cis-5'-deoxy-5'-(4-amino-2-butenyl)methylaminoadenosine.

5. A compound of claim 1, said compound being cis-5'-deoxy-5'-(4-amino-2-butenyl)aminoadenosine.

6. A compound of claim 1, said compound being cis-5'-deoxy-5'-(4-amino-4-carboxy-2-butenyl)methylaminoadenosine.

7. A compound of claim 1, said compound being cis-5'-deoxy-5'-(4-amino-4-carboxy-2-butenyl)aminoadenosine.

8. A compound of the formula

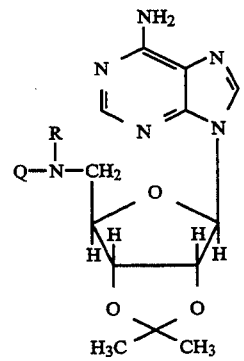

and the pharmaceutically acceptable salts thereof wherein

R represents H or a $C_{1-7}$ alkyl,

Q represents the moiety of the formula

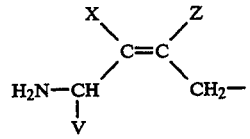

wherein

V represents H or —COOH,

X represents H, F, Cl, or Br, and

Z represents H, F, Cl, or Br.

* * * * *

UNITED STATES PATENT AND TRADEMARK OFFICE
CERTIFICATE OF CORRECTION

PATENT NO. : 5,416,076
DATED : May 16, 1995
INVENTOR(S) : Patrick Casara et al.

It is certified that error appears in the above-identified patent and that said Letters Patent is hereby corrected as shown below:

At column 4, line 8, the patent reads "trillate" and should read --triflate--.
At column 4, line 60, the patent reads "B-1" and should read --B-2--.
At column 10, line 9, the patent reads "19 mmol" and should read --1.9 mmol--.
At column 11, line 4, the patent reads "13 g" and should read --1.3 g--.
At column 14, line 17, the patent reads "5"-deoxy" and should read --5'-deoxy--.
At column 14, line 50, the patent reads "dihydropyrane" and should read --dihydropyran--.
At column 15, line 25, the patent reads "in uacuo" and should read --in vacuo--.
At column 15, lines 40-41, the patent reads "and., washed" and should read --and washed--.
At column 17, line 35, the patent reads "(16 g" and should read --(1.6 g--.
At column 18, line 66, the patent reads "Galabar" and should read --Calabar--.
At column 19, line 32, the patent reads "hemofiagellates" and should read --hemoflagellates--.
At column 21, line 34, the patent reads "and5'-deoxy" and should read --and 5'-deoxy--.

Signed and Sealed this

Second Day of July, 1996

BRUCE LEHMAN

Attest:

Attesting Officer            Commissioner of Patents and Trademarks